United States Patent [19]

Fossati

[11] Patent Number: 4,806,415
[45] Date of Patent: Feb. 21, 1989

[54] METHOD AND SYSTEM FOR DETERMINING THE PRESENCE OF ADENOSINE TRIPHOSPHATE OR FLAVIN MONONUCLEOTIDE

[75] Inventor: Piero Fossati, Buonarroti, Italy
[73] Assignee: Miles Inc., Elkhart, Ind.
[21] Appl. No.: 649,933
[22] Filed: Sep. 13, 1984

[30] Foreign Application Priority Data

Dec. 21, 1983 [IT] Italy ................ 49555 A/83

[51] Int. Cl.$^4$ ............................................. C12Q 1/54
[52] U.S. Cl. ...................................... 435/14; 435/15; 435/21; 435/25; 435/26; 435/28
[58] Field of Search ............... 435/14, 21, 25, 26, 435/28, 15

[56] References Cited

U.S. PATENT DOCUMENTS

| | | | |
|---|---|---|---|
| 4,238,565 | 12/1980 | Hornby et al. | 435/7 |
| 4,268,631 | 5/1981 | Ellis et al. | 435/190 |
| 4,278,761 | 7/1981 | Hastings et al. | 435/14 |
| 4,366,243 | 12/1982 | Rupchock et al. | 435/25 |
| 4,394,444 | 7/1983 | Cameron et al. | 435/14 |
| 4,604,356 | 8/1986 | Blake, II | 435/15 |

FOREIGN PATENT DOCUMENTS 0140899  11/1981  Japan ................ 435/14

OTHER PUBLICATIONS

Colowick, et al., Methods in Enzymology, vol. II, Academic Press Inc., (1955), pp. 673–675.
Enzyme Nomenclature, Elsevier Scientific Publishing Co., 1975, Amsterdam, pp. 180–181.
D. Jaworek, et al, in "Methods in Enzymatic Analysis", vol. 4, Sect. D, 2nd English Ed., H. U. Bergmeyer Ed., Academic Press, NY 2097 (1974).
W. Lamprecht, et al, in "Methods of Enzymatic Analysis", Sect. D. 2nd English Ed., H. U. Bergmeyer Ed., Academic Press, NY 2101 (1976).
J. Campbell, et al, Bioch. et Biophy. Acta, 397, 101–109(1975).
R. Spencer, et al, Biochem., 15(5):1043 (1976).
Burch et al, J. Biol. Chem., 175:457 (1948).
Koziol, Methods in Enzymology, 18 (Part B):253 (1971).
Mayhew & Wassink, Methods in Enzymology, 66 (Part E):217 (1980).
Knoblock, Methods in Enzymology, 18 (Part B):305 (1971).
Fazekas & Kokai, Methods in Enzymology, 18 (Part B):385 (1971).
Sugiura, et al, Chem. Pharm. Bull 29(5):1361 (1981).
Warburg & Christian, Biochem. Z. 298:150 (1938).
Ochoa, et al, Biochem. J. 33:2008 (1939).
Klein et al, J. Biol. Chem. 136:177 (1940).
Huennekens et al, Methods in Enzymology 3:950 (1957).
Scott et al, J. Biol. Chem. 238(12):3928 (1963).
Staal et al, Biochim. Biophys. Acta 185:39 (1969).
Visser & Veeger, Biochim. Biophys. Acta 206:224 (1970).

Primary Examiner—Robert J. Warden
Assistant Examiner—Stephen C. Wieder
Attorney, Agent, or Firm—Konrad H. Kaeding

[57] ABSTRACT

An enzymatic determination of one of the co-enzymes adenosine triphosphate (ATP) or flavin mono-nucleotide (FMN) based on the use of an flavine adenine dinucleotide (FAD) synthetase-active system in conjunction with the other coenzyme to generate FAD. The generated FAD can then be measured to determine the ATP or FMN concentration in the sample. Preferably, the generated FAD is measured by combination with a corresponding apoenzyme, preferably apo (glucose oxidase), and measuring the activity of the enzyme produced. The resultant active enzyme is preferably measured in a manner which results in a colorimetric response. The present invention provides an ATP or FMN assay which combines the sensitivity of bioluminescent assays with the convenience of a colorimetrically detectable response.

12 Claims, No Drawings

METHOD AND SYSTEM FOR DETERMINING THE PRESENCE OF ADENOSINE TRIPHOSPHATE OR FLAVIN MONONUCLEOTIDE

BACKGROUND OF THE INVENTION

1. Field of the Invention

This invention relates to assay methods, and reagent means for use therein, for the determination of one of the coenzymes adenosine triphosphate (ATP) or flavin mononucleotide (FMN) in a liquid medium. In particular, this invention relates to an enzymatic assay for ATP or FMN based on the use of a flavin adenine dinucleotide (FAD) synthetase-active preparation to produce FAD. FAD indicator systems are used to generate a detectable, usually colorimetric, response. FAD synthetase is formally designated as ATP:FMN Adenylyl Transferase (EC 2.7.7.2) by the International Committee of Enzyme Nomenclature.

2. Description of the Prior Art

The production of ATP is a common goal of both anaerobic and aerobic metabolitic activity. Determination of ATP is a direct indication of life, and is a useful index of the presence of microbial biomass and microbiological activity. However, the concentration of ATP in biological fluids is often only $10^{-9}$ moles/liter (nanomolar) to $10^{-12}$ moles/liter (picomolar) or even less, so that detection requires highly sensitive ATP assays.

The enzymatic determination of adenosine phosphates by spectrophotometric methods involving pyridine nucleotides has come into general use because of its simplicity compared with paper or column chromatography methods.

A well known ultraviolet photometric method for the determination of ATP involves the following sequence of reactions [Jaworek, D., et al., in "Methods of Enzymatic Analysis", Section D, 2nd English Ed., H. U. Bergmeyer Ed., Academic Press, New York 2097, (1974)]:

$$\text{ATP} + \text{3-Phosphoglycerate} \xrightarrow{\text{Phosphoglycerate kinase}}$$

1,3-Diphosphoglycerate + adenosine diphosphate (ADP)

$$\text{1,3-diphosphoglycerate} + \text{NADH} + \text{H}^+ \xrightarrow{\text{Glyceraldehyde 3-phosphate dehydrogenase}}$$

Glyceraldehyde-3P + inorganic phosphate (P$_i$) + nicotinamide adenine dinucleotide where the decrease in absorbance of reduced nicotinamide adenine dinucleotide (NADH) is monitored at 340 nanometers (nm). The NADH disappearance can also be monitored by its native fluorescence which increases the assay sensitivity up to micromolar ($10^{-6}$ moles/liter) levels of ATP. However, the method suffers from lack of specificity as other nucleoside triphosphates, including guanosine triphosphate, inosine triphosphate, and uridine triphosphate, can be measured as ATP.

The hexokinase/glucose-6-phosphate dehydrogenase method [Lamprecht, W., et al., in "Methods of Enzymatic Analysis" Section D, 2nd English Ed., H. U. Bergmeyer Ed., Academic Press, New York 2101, (1974)] has also proven valuable in the enzymatic determination of ATP. Highly purified enzymes are mandatory to obtain good specificity with this method.

Another interesting approach involves amplifying sensitivity through a reaction mechanism that casts the analyte itself into a cycling role so that a stoichiometric amount of product is formed and accumulated every time the analyte is cycled [Campbell, J., et al., Bioch. et Biophy. Acta, 397, 101–109 (1975)]. For example, the ATP can be determined by cycling between two enzyme catalyzed reactions to yield a product, e.g., (pyruvate kinase and hexokinase to glucose-6-phosphate), which product is determined by a third enzymatic reaction:

(a) cycling reaction:

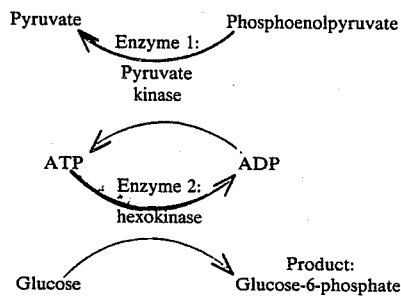

(b) monitoring reaction:

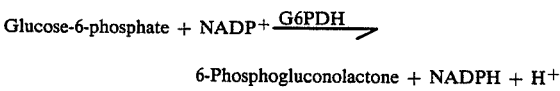

However, the manipulations required are too cumbersome for routine use.

The concentration of adenosine phosphates in biological fluids can also be determined by bioluminescent methods. In particular ATP in biological fluids can be measured by monitoring the emitted light produced by the following reactions:

$$\text{ATP} + \text{Luciferin} \xrightarrow{\text{Luciferase/Mg}^{++}} \text{Adenyl Luciferin}$$

$$\text{Adenyl Luciferin} + \text{O}_2 \longrightarrow \text{Adenyl oxyluciferin} + \text{light}$$

Such bioluminescent methods are presently preferred as their higher sensitivity allows for an ATP assay in the nanomolar to picomolar range. While an improvement over conventional techniques, emitted light measurement is limited in routine use both because dedicated instrumentation is required for reading and because of the lack of automated instrumentation for sample processing. Therefore, there is a need for improved methods for determining ATP.

Hornby, et al., U.S. Pat. No. 4,238,565, describe the use of an organic prosthetic group, such as FAD, which will combine with an apoenzyme (both inactive components) to form a holoenzyme (active), as a label in a specific binding assay.

SUMMARY OF THE INVENTION

The present invention couples the generation of FAD by the action of FAD synthetase on ATP and FMN with detection of the generated FAD, usually by enzymatic means. It has been found that the concentration of the coenzyme ATP or FMN in an aqueous liquid sample can be determined by combining the sample with a test system comprising the other of those coenzymes and an enzyme system having FAD synthetase activity, and subsequently determining the FAD produced. Since ATP and FMN are coenzymes in many biological reactions, their presence is an indication of the presence of biosystems in a sample. Further, detection of their generation or consumption in specific enzymatic reactions can be used to aid in the diagnosis of particular clinical states. In a preferred embodiment the enzyme system having FAD synthetase activity is FAD synthetase (EC 2.7.7.2) and an appropriate metal cation.

Preferably, the FAD produced is determined by adding an apoenzyme of FAD and subsequently determining the activity of the resulting active enzyme (holoenzyme). An FAD determination which produces an enzyme provides a more sensitive ATP assay than other methods of FAD determination. Each molecule of enzyme produced can catalyze the conversion of a suitable substrate to produce thousands of molecules of product. A reaction system can be chosen so that action of the produced active enzyme on a substrate results in a detectable response. This enzymatic conversion amplifies the detectable response to allow an ATP or FMN assay of the sensitivity required for diagnostic assays.

The use of apo(glucose oxidase) to determine FAD by measurement of glucose oxidase activity is particularly preferred. Glucose oxidase activity is advantageously determined by adding glucose, a peroxidatively active substance and an indicator which gives a detectable response. Indicators can be selected to provide a color change.

Detecting FAD through its coupling with the apo(glucose oxidase) system above or other colorimetric apoenzyme system provides an assay for ATP or FMN with which combines nanomolar sensitivity with a convenient colorimetric determination.

DESCRIPTION OF THE PREFERRED EMBODIMENTS

The present invention involves two principal steps: (1) generation of FAD in a liquid test sample containing one of the coenzymes ATP or FMN and (2) determination of the FAD produced. Generation of FAD is accomplished by use of an enzyme system with FAD synthetase activity and the other of the coenzymes. FAD measurement is most advantageously accomplished by a detection system which utilizes an apoenzyme requiring FAD for its activity and subsequently measuring the activity of the enzyme produced.

The assay can be used to determine ATP or FMN as the analyte of interest or to determine any analyte involved in a reaction which will generate or consume ATP or FMN.

Diagnostic applications

Many clinical applications deal with measurement of adenosine nucleotide phosphates either as a material present in the sample or as derived from coupled reactions.

Two examples of the diagnostic application of the ATP monitoring are described: one in which the ATP present in the sample is directly monitored, the other in which ATP derived from a coupled reaction is assayed. Other possible applications are listed.

Bacteriuria screening (direct assay)

Significant bacteriuria has been defined as the presence of $10^5$ viable bacteria per milliliter (ml) in freshly voided specimens of urine. As urine specimens form a major part of the workload in routine microbiological laboratories, particular attention should be given to the development of rapid screening tests for bacteriuria which provide results more rapidly and less expensively than the traditional culture methods. The present invention provides such a rapid, inexpensive screening test.

The utilization of the ATP assay for bacteriuria is based on the fact that each cell type has relatively constant levels of ATP under normal conditions (around $5 \times 10^{-18}$ to $8 \times 10^{-17}$ mole/cell). Extensive literature shows bacteriuria is correlated with ATP content.

Creatine kinase-B isoenzyme activity monitoring (coupled assay)

Creatine kinase (CK) is present in human tissue as three different isoenzymes: CK-MM (muscle type), CK-BB (brain type) and CK-MB (myocardial type). An assay of total creatine kinase activity in human sera is used in the detection and management of acute myocardial infarction: Increased diagnostic specificity may be obtained by assaying the CK-MB isoenzyme.

An inhibiting antibody directed against the M subunit of human CK, leaving the B subunit unaffected, has been used in the ultraviolet spectrophotometric assay of CK-B activity. This method is considered to be less time consuming and more suitable for routine work than previous methods (i.e., electrophoresis, ion exchange chromatography, etc.). However, the sensitivity of the indicator system (NADH) limits the applicability of the immunochemical/UV method to serum samples with total CK levels several times above the upper limit of the normal range.

A CK-B subunit assay of greater sensitivity can be achieved through ATP generation according to the following scheme:

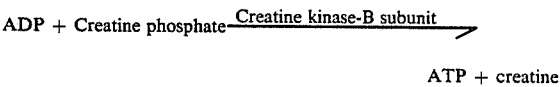

ADP + Creatine phosphate $\xrightarrow{\text{Creatine kinase-B subunit}}$

ATP + creatine and the subsequent assay of ATP by the present invention.

Due to the inherent sensitivity of the ATP assay proposed, this procedure would allow the assay of B subunit activity in serum from healthy individuals, thus enabling an early accurate diagnosis of even very small myocardial damage.

| Additional applications of ATP assay | |
|---|---|
| Compound | Method |
| Metabolites | |
| Cyclic adenosine monophosphate (AMP) | formation of ATP by phosphodiesterase-myokinase-pyruvate kinase |
| Creatine Phosphate | formation of ATP by creatine kinase |
| Glucose | consumption of ATP by hexokinase |
| Guanosine triphosphate | formation of ATP by nucleoside diphosphate kinase |
| AMP | formation of ATP by myokinase-pyruvate kinase |
| Triglycerides | consumption of ATP by lipase-glycerokinase |
| Enzymes | |
| ATP-sulphurylase | formation of ATP from Adenosine sulfate |
| ATP-ase | consumption of ATP |
| Myokinase | consumption of ATP |
| Pyruvate kinase | formation of ATP |
| 5'-Nucleotidase | consumption of ATP |
| Hexokinase | consumption of ATP |
| Guanosine mono- | consumption of ATP by |

-continued

| Additional applications of ATP assay | |
|---|---|
| Compound | Method |
| phosphate phosphodiesterase | guanylate kinase |
| Immunology | |
| Specific Proteins binding reactions | Ligand-ATP monitoring (see U.S. Pat. No. 4,230,797 and British Pat. Spec. 1,548,741 and 1,552,607) |
| Miscellaneous | |
| Sperm viability | Direct ATP monitoring |
| Erythrocyte viability | Direct ATP monitoring |
| Platelets viability | Direct ATP monitoring |
| Tissue and cell culture test | Direct ATP monitoring |
| Adenylate energy charge | Generation of ATP by ADP + AMP |
| Susceptibility of germs to antibiotics | Direct ATP monitoring |
| Determination of antibiotics levels in biological fluids | Monitoring of ATP generated by an appropriate microbial strain |
| Microbial contamination in foods or industrial products | Monitoring of ATP generated by an appropriate microbial strain |

As used herein, the phrase "enzyme system having FAD synthetase activity" is intended to mean a composition which comprises an enzyme and which catalyzes the reaction of ATP and FMN to produce FAD. Such system can comprise in addition to the enzyme, any desirable or necessary cofactors for the condensation reaction. The FAD synthetase active preparation is preferably prepared from *Brevibacterium ammoniagenes* and isolated and purified according to the procedures of R. Spencer et al., Biochemistry vol. 15, no. 5, at p. 1044 (1976). This particular enzyme preparation requires a cation chosen from the group $Mg^{+2}$, $Co^{+2}$, $Ni^{+2}$, $Mn^{+2}$ or $Zn^{+2}$ for activity; the preferred cation being $Mg^{+2}$. An improvement of the Spencer et al method which provides a significantly more pure enzyme preparation is described in the U.S. Pat. No. 4,604,305 entitled "Purification of Flavin Adenine Dinucleotide Synthetase" filed on even date herewith and assigned to Miles Laboratories, Inc., which is incorporated herein by reference.

In accordance with the present invention, FAD can be determined or measured in the liquid test sample by any available means including fluorometric methods [Burch et al, *J. Biol. Chem.* 175: 457 (1948); Koziol, *Methods in Enzymology* 18(*Part B*): 253 (1971); and Mayhew and Wassink, *Methods in Enzymology* 66-(*Part E*): 217 (1980)], polarographic methods [Knoblock, *Methods in Enzymology* 18(*Part B*): 305 (1971)]; spectrophotometric methods [Fazehus and Kokai, *Methods in Enzymology* 18(*Part B*): 385 (1971)]; and in general any method available to one working the field.

It is preferred to determine the generated FAD by its ability to combine with an inactive apoenzyme to produce a detectable holoenzyme. Useful apoenzymes include apo(glucose oxidase) [Ellis et al. U.S. Pat. No. 4,268,631], apo(xanthine oxidase) [Sugiura et al, *Chem. Pharm. Bull.* 29: 1361(1981)], apo(amino acid oxidase) [Warburg and Christian, *Biochem. Z.* 298: 150(1938); and see Ocha et al. *Biochem. J.* 33: 2008 (1939), Klein et al., *J. Biol. Chem.* 136: 177 (1940), and Hunnekens et al., *Methods in Enzymology* 3: 950 (1957)], apo(glutathione reductase) [Scott et al, Scott et al., *J. Biol. Chem.* 238: 3928 (1963) and Staal et al, *Biochim. Biophys. Acta,* 185: 39 (1969)], and apo(lipoamide dehydrogenase) [Visser and Beeger, *Biochim. Biophys. Acta,* 206: 224 (1970)]. Most preferred is apo(glucose oxidase).

A variety of methods can be used to determine the activity of the resulting enzyme. These will be evident to the worker in the field. Where glucose oxidase is measured, such available methods include: potentiometric methods with an oxygen electrode, following the direct oxygen disappearance or following the indirect production of oxygen through a coupled reaction using catalase; visible or ultraviolet spectrophotometric and chemiluminescent or fluorometric techniques, by appropriately coupling reactions suitable for hydrogen peroxide detection. The most preferred apo(glucose oxidase) test system additionally comprises glucose as enzyme substrate, and, as the indicator system, a peroxidatively active substance and a photogen which provides the optical signal.

The preferred reaction scheme by which the present invention is accomplished is:

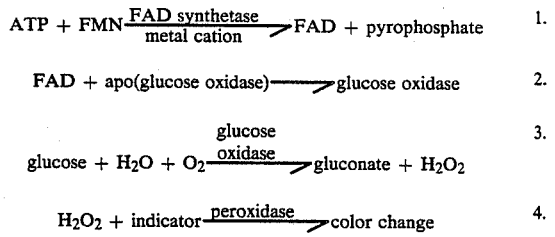

Peroxidatively active substances are well known in the art and include substances from various organic and inorganic sources. Plant peroxidases, such as horseradish peroxidase or potato peroxidase, can be used. Inorganic compounds having peroxidase activity include iodides, such as sodium and ammonium iodides, and molybdates can be used. In addition, urohemin and a number of other porphyrin substances having peroxidative activity can be used. Other substances which are not enzymes, but which have peroxidative activity, include such compounds as iron sulfocyanate, iron tannate, ferrous ferrocyanide, potassium chromic sulfate and the like.

Likewise, a wide variety of useful photogens are known in the art to provide a detectable optical signal in the presence of or upon reaction with hydrogen peroxide and the peroxidatively active substance. Such photogens include chromogens or color indicator dyes, for example, ortho-tolidine, benzidine, syringaldazine, diaminofluorene, and tetramethylbenzidine, and related derivatives, and also include coupled dye systems such as those conventionally referred to as Trinder reagents, e.g., a phenol and 4-aminoantipyrine. Other useful photogens are fluorogenic peroxidase substrates such as scopoletin (6-methoxyumbelliferone), para-hydroxyphenylacetic acid, and various fluoroscein derivatives such as diacetyldichlorofluorescein (U.S. Pat. No. 4,269,938). Chemiluminescers such as luminol, isoluminol, pyragallol, and their various derivatives and analogs, can also be used as the photogen.

The test system can include other components as well such as buffers, diluents, stabilizers and the like. Suitable buffers include phosphate, N-2-hydroxyethylpiperazine-N'-2-ethanesulfonic acid (HEPES), 3-(N-morpholino)propanesulfonic acid (MOPS), Tris(hydroxymethyl)-aminomethane (TRIS), N-tris-(hydroxymethyl-methyl-2-aminoethanesulfonic acid (TES) and N-2-hydroxyethylpiperazine propane sulfonic acid (EPPS). Also, where the rupture of cells or digestion of cellular debris is desired for performing the assay, detergents, proteolytic enzymes, and like materials can also be included in the test system.

|  | Working Range | Preferred Range |
|---|---|---|
| nonanalyte coenzyme ATP or FMN | 1-1000 | 5-100 micromoles/l |
| FAD synthetase | 0.05-100 | 0.1-10 I.U./ml |
| cation (Mg$^{+2}$) | 0.1-20 | 1-15 millimoles/l |
| apoenzyme: apo(glucose oxidase) | 1-1000 | 5-100 mg/l |
| enzyme substrate: (glucose) | 0.01-10 | 0.05-2 moles/l |
| Peroxidatively active agent: (peroxidase) | 0.01-100 | 0.1-10 I.U./ml |
| indicator | 0.01-10 | 0.1-3 millimoles/l |
| buffer and pH | 10-1000 pH 4-10 | 20-200 millimoles/l pH 5-8 |

I.U./ml is defined as International Units per milliliter of stock solution. The International Unit (I.U.) is a unit of enzyme activity, one I.U. is the enzyme activity required to catalyze the conversion of one micromole (μmol) of substrate per minute under specified conditions of pH and temperature. As used here, one (1) I.U. of FAD synthetase catalyzes the conversion one micromole of FMN per minute at pH 7.5 and 37° C. One (1) I.U. of peroxidase catalyzes the conversion of one micromole of peroxide per minute at pH 6.9, 25° C.

The ATP or FMN sensitive test system can be in any convenient form such as a test kit, a test composition admixture, or a test device. The test composition admixture or the test kit components can be liquid, usually aqueous solutions; dry powders, tablets, or the like; or in the form of gels, films and so forth. A preferred test system format is the reagent strip test device wherein the test system is incorporated with a carrier matrix. The carrier may take the form of either bibulous or nonbibulous, porous or nonporous, matrices which are insoluble in and maintain their structural integrity when exposed to water or other fluids of analytical interest. Suitable bibulous matrices which can be used include absorbent paper, polymeric films and gels, cellulose, wood, synthetic resin fleeces, woven and nonwoven fabrics, and the like. Nonbibulous matrices include glass fiber and organoplastic materials, such as polypropylene and the like. The carrier matrix can be soaked, immersed in, sprayed or printed with the liquid reagent composition and the carrier matrix thereafter dried by suitable means, such as ambient or forced air drying to leave the dry reagent/matrix combination. The matrix can be advantageously affixed to an insoluble support member such as an organoplastic strip, e.g., polystyrene, by suitable means, such as double faced adhesive tape, for ease of use.

When in the form of an FAD generating and glucose oxidase detection reagent strip device, the present test system provides a simple and convenient means for detecting ATP or FMN. In contrast with the prior art techniques, the present reagent strip device provides an assay result upon contact with the test sample. The generated optical signal is readily read by an instrument or, where appropriate, such as where color changes are generated, observed by the technician. The reference signal can be stored within the instrument or can be in the form of an observable standard such as a color chip or chart, and the comparison made internally by the instrument or by the human observer. Such a simple, straight forward, rapid method for detecting ATP or FMN in liquids, particularly biological fluids, has not been available previously.

The present invention will now be illustrated, but is not intended to be limited, by the following examples.

EXAMPLE

Tests were performed on the complete system of reactions, using aqueous solutions of ATP as test sample. The 3,5-dichloro-2-hydroxybenzenesulfonic acid/4-aminophenazone chromogenic system proved to be reliable for kinetic monitoring of glucose oxidase activity.

Materials

FAD synthetase isolated from *Brevibacterium ammoniagenes* and purified according to the procedure of R. Spencer et al. supra.

Apo(glucose oxidase) prepared according to Ellis et al., U.S. Pat. No. 4,268,631.

Peroxidase (horseradish)

| SOLUTION #1 FAD-synthetase | |
|---|---|
| Phosphate buffer, pH 7.0; | 50 mM |
| MgCl$_2$; | 8 mM |
| Flavin monophosphate; | 0.05 mM |
| FAD synthetase; | 1.0 I.U./ml |
| SOLUTION #2 Apo(glucose oxidase) | |
| Apo(glucose oxidase) (0.8 moles of FAD binding sites/ml) | 66 μg/ml |
| Phosphate buffer, pH 7.0; | 50 mM |
| SOLUTION #3 Chromogenic System | |
| Phosphate buffer, pH 7.0; | 50 mM |
| 4-aminophenazone; | 0.08 mM |
| Peroxidase; | 0.5 I.U./ml |
| 3,5-dichloro-2-hydroxy-benzenesulfonic acid; | 2 mM |
| Glucose; | 0.2 M |
| SOLUTION #4 ATP aqueous (samples) | |
| The ATP solutions used were at concentrations corresponding, in the final reaction volume, to 9; 27; 54; 90; 135; 180; and 360 picomoles/liter. | |

Units: International units per milliliter (I.U./ml) millimolar (mM), micromolar (μM), micrograms per milliliter (μg/ml).

Test Procedure

A 3-step procedure was used: First, the ATP in the aqueous solution samples was converted, by FAD-synthetase in the presence of flavine monophosphate, to FAD (0.1 ml of different ATP concentrations, Solution #4, were added to 0.9 ml of Solution #1 and let stand at room temperature in the dark for 18 hours); second, the FAD produced in the first step was incubated with the apoenzyme to restore the glucose oxidase activity (0.2 ml of the first step mixture was added to 0.2 ml of Solution #2 and let stand at room temperature for 30 minutes); third, the glucose oxidase activity was kinetically monitored (0.02 ml of the second step was added to 2 ml of the chromogenic Solution #3 and, after exactly 15 minutes at 25° C., the absorbance was measured at 510 nm.

A parallel reagent blank was prepared by substituting 0.1 ml of distilled water for the ATP Solution #4 in the first step and then the same procedure was followed. The absorbance of the reagent blank was subtracted from the absorbance of the sample.

Data obtained showed linear response at all ATP concentrations tested. Although the reported procedure utilized multiple steps, a single reagent system, single step assay is feasible as the reagents and enzymes are compatible.

Another chromogenic system, 3,3′,5,5′-tetramethylbenzidine (TMB), proved reliable for both kinetic and end-point monitoring of glucose oxidase activity. Tests were performed with aqueous solutions of FAD.

The following solutions were used:

| SOLUTION #1 Apo(glucose oxidase) | |
|---|---|
| Apo(glucose oxidase) (3.1 moles of FAD binding sites/ml) | 0.26 mg/ml |
| Phosphate buffer, pH 7.0; | 50 mM |
| SOLUTION #2 Chromogenic System | |
| 2-(N—Morpholino)ethane-sulfonic acid (MES) pH 6.0 | 70 mM |
| Tetramethyl benzidine hydrochloride (TMB.2HCl) | 0.5 mM |
| Peroxidase; | 0.5 I.U./ml |
| Glucose | 0.2 M |
| Triton X-100 ® surfactant; (Rohm & Haas Inc, Philadelphia, PA) | 0.15% (w/v) |
| SOLUTION #3 Stopping reagent | |
| HCl; | 4 Normal (N) |
| SOLUTION #4 FAD aqueous (samples) | |
| The FAD solutions used were at concentrations, corresponding in the final reaction volume, to 17; 34; 68; 136; 205; 341; and 478 picomoles/liter. | |

Test Procedure

A one-step procedure was used. Solutions #1, #2, and #4 were combined. The glucose oxidase activity restored by the FAD recombination with apoglucose oxidase was monitored directly either by a kinetic procedure, reading the increase of the chromogen absorbance at 650 nanometers (nm), or by an end point procedure with the addition of hydrochloric acid (Solution #3) after allowing the reaction to proceed exactly 30 minutes at 25° C., reading the chromogenic absorbance at 450 nm. In either the kinetic or endpoint procedure apo(glucose oxidase) is used to start the reaction.

A parallel reagent blank was carried out by substituting distilled water for FAD in the FAD samples; the reagent blank reading so obtained was subtracted from the sample absorbance.

Data obtained by both procedures showed linear response at all the FAD concentrations tested.

The same principle can be applied to other adenine nucleotide phosphates assay, by coupling reactions able to produce ATP, e.g., adenosine diphosphate (ADP) can be assayed by first converting it to ATP by the pyruvate kinase catalyzed reaction;

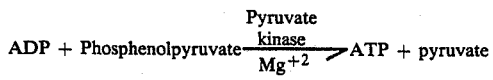

PREPARATION OF TEST DEVICE

Test devices incorporating the test composition according to the present invention are prepared and used in testing for the presence of ATP or FMN in body fluids such as blood or urine.

The impregnating solution is prepared according to the following formulation:

| FAD synthetase | 1.0 I.U./ml |
|---|---|
| MgCl$_2$ | 8 mM |
| Apo(glucose oxidase) | 66 μg/ml |
| 4-aminophenazone | 0.08 mM |
| peroxidase | 0.5 I.U./ml |
| 3,5-dichloro-2-hydroxy benzene sulfonic acid | 2 mM |
| glucose | 2 M |
| phosphate buffer pH 7.0 | 100 ml |

Sheets of Whatman No. 17 filter paper (Whatman Inc. Clifton, NJ) are impregnated to saturation with the above solution and dried at 60° C. (Centigrade).

Alternatively the impregnation is accomplished with two solutions, one aqueous solution comprising FAD synthetase, MgCl$_2$, apo(glucose oxidase), peroxidase, and phosphate buffer; and a second organic solution comprising the indicators, 4-aminophenazone and 3,5-dichloro-2-hydroxybenzene sulfonic acid, in a suitable organic solvent. After impregnation with one solution, the filter paper is dried at 60° C. before the second impregnation. Final drying is also accomplished at 60° C.

In either case the Whatman sheets containing the dried residue of the impregnating solutions are cut to 2.5 millimeters (mm)×2.5 mm to form test devices. The test devices are then backed with double-faced adhesive tape and fixed thereby to plastic handles.

The test device is most advantageously used by momentarily dipping it in a sample (e.g., an aqueous ATP or FMN solution or a body fluid sample) or by otherwise introducing the sample onto the carrier matrix. A detectable color change results when ATP or FMN is present. Since the amount of color developed depends on ATP or FMN concentration, a semiquantitative assay is made possible through use of appropriate color charts, and a quantitative assay is made possible through use of an appropriate reflectance reading instrument.

While the above disclosure has primarily been directed at detection of ATP, it is understood that similar results can be achieved by using ATP as the coenzyme to detect FMN.

Although the invention has been described with a certain degree of particularity, it is understood that the present disclosure has been made only by way of example and that numerous changes in the details can be resorted to without departing from the scope of the invention.

What is claimed is:

1. A reagent system for the determination of a coenzyme selected from the group consisting adenosine triphosphate and flavin mononucleotide in an aqueous liquid sample, comprising:
   (a) a coenzyme selected from adenine flavin mononucleotide triphosphate and flavin mononucleotide, one of which is the substance to be determined and the other of which is a component of the reagent system;
   (b) an enzyme preparation having flavin adenine dinucleotide synthetase activity; and
   (c) apo(glucose oxidase).

2. The reagent system of claim 1, additionally comprising glucose, peroxidase and a chromogenic indicator capable of providing a detectable colorimetric response in the presence of hydrogen peroxide and peroxidase.

3. An analytical method for determining adenosine triphosphate ("ATP") in picomole concentrations, said method comprising the steps of:
  combining a liquid sample with a reagent system, said system comprising in a single solution:
  flavin mononucleotide ("FMN");
  flavin adenine dinucleotide ("FAD") synthetase;
  apo(glucose oxidase);
  a peroxidatively active substance;
  glucose;
  a metal cation; and
  a photogen, whereby said photogen provides a detectable optical response in the presence of hydrogen peroxide and the peroxidatively active substance, and
  detecting the optical response said response being an indication of the amount of ATP down to picomole concentrations in said liquid sample.

4. The analytical reagent system of claim 3 wherein the metal cation comprises magnesium ion.

5. A reagent test strip for determining adenosine triphosphate ("ATP") in concentrations as low as a picomole per liter, said strip having a carrier matrix comprising the analytical reagent system of claim 4.

6. An analytical assay method comprising the method of claim 3 whereby the determination of ATP is used to assay biological activities or substances which relate to the existence of ATP.

7. The analytical assay method of claim 6, whereby said method is used to assay creatin kinase, cyclic adenosine monophosphate, creatine phosphate, glucose, guanosine triphosphate, triglycerides, ATP-sulphurylase, ATP-ase, myokinase, pyruvate kinase, 5'-nucleotidase, hexokinase, guanosine monophosphate phosphodiesterase, protein binding reactions relating to the existence of ATP, sperm viability, erythrocyte viability, platelet viability, or tissue or cell viability.

8. An analytical method for determining flavin mononucleotide ("FMN") in picomole concentrations, said method comprising the steps of:
  combining a liquid sample with a reagent system, said system comprising in a single solution:
  adenosine triphosphate ("ATP");
  flavin adenine dinucleotide ("FAD") synthetase;
  apo(glucose oxidase);
  a peroxidatively active substance;
  glucose;
  a metal cation; and
  a photogen, whereby said photogen provides a detectable optical response in the presence of a hydrogen peroxide and the peroxidatively active substance, and
  detecting the optical response said response being an indication of the amount of FMN down to picomole concentrations in said liquid sample.

9. The analytical reagent system of claim 8 wherein the metal cation comprises magnesium ion.

10. A reagent test strip for determining flavin mononucleotide ("FMN") in concentrations as low as a picomole per liter, said strip having a carrier matrix comprising the analytical reagent system of claim 9.

11. An analytical reagent system for determining adenosine triphosphate ("ATP") in picomole concentrations, said reagent system comprising:
  flavin mononucleotide ("FMN");
  flavin adenine dinucleotide ("FAD") synthetase;
  apo(glucose oxidase);
  a peroxidatively active substance;
  glucose;
  a metal cation; and
  a photogen, whereby said photogen provides a detectable optical response in the presence of a hydrogen peroxide and the peroxidatively active substance.

12. An analytical reagent system for determining flavin mononucleotide ("FMN") in picomole concentrations, said reagent system comprising:
  adenosine triphosphate ("ATP");
  flavin adenine dinucleotide ("FAD") synthetase;
  apo(glucose oxidase);
  a peroxidatively active substance;
  glucose;
  a metal cation; and
  a photogen, whereby said photogen provides a detectable optical response in the presence of a hydrogen peroxide and the peroxidatively active substance.

* * * * *